(12) United States Patent
Fuentevilla

(10) Patent No.: US 8,021,150 B2
(45) Date of Patent: Sep. 20, 2011

(54) METHOD FOR DENTAL IMPLANT PLACEMENT

(75) Inventor: Roberto Carrillo Fuentevilla, Nuevo Leon (MX)

(73) Assignee: Roberto Carrillo (MX)

( * ) Notice: Subject to any disclaimer, the term of this patent is extended or adjusted under 35 U.S.C. 154(b) by 195 days.

(21) Appl. No.: 12/209,115

(22) Filed: Sep. 11, 2008

(65) Prior Publication Data

US 2009/0176182 A1    Jul. 9, 2009

Related U.S. Application Data

(60) Provisional application No. 60/971,522, filed on Sep. 11, 2007.

(51) Int. Cl.
*A61C 19/04*    (2006.01)
*A61C 8/00*    (2006.01)
(52) U.S. Cl. .......................................... 433/72; 433/173

(58) Field of Classification Search ................. 433/2, 3, 433/18, 72, 75, 76, 173, 174; 606/96
See application file for complete search history.

(56) References Cited

U.S. PATENT DOCUMENTS

| | | | | |
|---|---|---|---|---|
| 3,547,121 A | * | 12/1970 | Cherry | 604/116 |
| 5,769,636 A | * | 6/1998 | Di Sario | 433/213 |
| 5,954,769 A | * | 9/1999 | Rosenlicht | 623/16.11 |
| 6,592,368 B1 | * | 7/2003 | Weathers, Jr. | 433/76 |
| 7,637,741 B2 | * | 12/2009 | Devincenzo et al. | 433/174 |
| 2003/0044745 A1 | * | 3/2003 | Kim | 433/4 |
| 2006/0251220 A1 | * | 11/2006 | Young et al. | 378/204 |
| 2006/0257817 A1 | * | 11/2006 | Shelton | 433/75 |
| 2008/0026338 A1 | * | 1/2008 | Cinader | 433/29 |
| 2008/0032258 A1 | * | 2/2008 | Kyung et al. | 433/75 |

* cited by examiner

*Primary Examiner* — John J Wilson
(74) *Attorney, Agent, or Firm* — Caesar, Rivise, Bernstein, Cohen & Pokotilow, Ltd.

(57) ABSTRACT

Dental implant placement may be facilitated using a guide and/or placement system. The guide may allow an appropriate position for a dental implant to be determined. The placement system may position the guide in a patient.

4 Claims, 8 Drawing Sheets

Marked position

METHOD FOR DENTAL IMPLANT PLACEMENT

CLAIM OF PRIORITY

This application claims priority under 35 USC §119 to U.S. Provisional Patent Application Ser. No. 60/971,522, filed on Sep. 11, 2007, the entire contents of which are hereby incorporated by reference.

TECHNICAL FIELD

The present invention relates to dental implant placement, more particularly, to dental miniscrew implant placement.

BACKGROUND

Dental implants are commonly used in various orthodontic applications. For example, miniscrews are often used as anchors. The placement of miniscrews in a patient's mouth is difficult due to the small area in which undesirable areas (e.g., nerves, roots, regions bad gums, tooth structures) are not present. Often, use of placement aides requires invasive coupling of the placement aides to a patient, which may increase patient recovery time and/or trial and error positioning of placement aides by a skilled user.

SUMMARY

In various implementations, dental implant placement may be facilitated. Incorrect and/or inaccurate placement of dental implants (e.g., in the alveolar bone) may reduce the effectiveness of the dental implants and increase patient discomfort. The system may include one or more guides and/or placement systems to increase the accuracy of dental implant placement. The guide may be radio-opaque and include apertures. The placement system may couple the guide to the patient during use, and an appropriate position of the dental implant may be determined using the guide. The determined appropriate position may be marked on the patient. The guide and/or placement system may be removed and the dental implant (e.g., miniscrew) may be positioned in the patient.

In one general aspect, an orthodontic placement system may include a base adapted to couple to a portion of a mouth and a guide including more than one positioning apertures. A position for a dental implant may be identifiable using the positioning apertures. The system may include an adjustment member that may be coupled to the guide and/or allow a position of the guide, relative to the base, to be modified. The system may also include a coupling member that may couple the adjustment member to the base.

Various implementations may include one or more or none of the following features. The base may include one or more wire apertures, and at least one of the apertures may receive at least a portion of the coupling member to couple the adjustment member to the base. The base may include one or more wire apertures, and at least one of the wire apertures may be configured to receive an archwire. The guide may include at least one of a grid or mucogingival junction members. One or more of the positioning apertures may be at least one of square-shaped, rectangular-shaped, c-shaped, triangular-shaped, oval-shaped, or circular-shaped. The adjustment member may include a deformable material, and wherein positioning the guide may include deforming the adjustable member. The base may be adapted to couple to a bracket to couple to a portion of a mouth. The base may be adapted to directly couple to a portion of a mouth. A dental implant may be positioned, using at least one of the positioning apertures, in the portion of a mouth.

In another general aspect, an orthodontic placement kit may include a base adapted to couple to a portion of a mouth, one or more types of guides, an adjustment member coupled to each of the guides, and a coupling member configured to couple the adjustment member to the base. Each guide may include more than one positioning aperture, and a position for a dental implant may be identifiable using the positioning apertures. An adjustment member may allow a position of the guide, relative to the base, to be modified.

Various implementations may include one or more or none of the following features. The base may include one or more wire apertures. The kit may include an acrylic base configured to couple to a portion of a mouth and retain the guide. The kit may include more than one base and more than one coupling member.

In another general aspect, a guide, including more than one positioning aperture, may be coupled to a base, a position of the guide relative to the base may be adjusted, and a position for a dental implant may be identified using one or more of the positioning apertures.

Various implementations may include one or more or none of the following features. The base may be coupled to a portion of a mouth. Adjusting a position of the guide relative to the base may include deforming an adjustment member coupled to the guide, where the adjustment member couples the guide to the base. Identifying a position for a dental implant may include obtaining a radiograph of a guide positioned in a mouth. A dental implant may be disposed proximate to or at least partially through an aperture of the guide.

An orthodontic placement system may include a guide, that includes more than one positioning aperture, and a placement system that may couple the guide to a portion of a mouth. A position for a dental implant may be identifiable using the positioning apertures.

Various implementations may include one or more or none of the following features. The system may include an adjustment member coupled to the guide, where the adjustment member may be adapted to allow a position of the guide, relative to the base, to be modified. The placement system may couple the adjustment member to a portion of the mouth. The placement system may include an acrylic base adapted to couple to a portion of a mouth and retain the guide. The placement system may include an adhesive adapted to couple to a portion of a mouth and retain the guide.

The details of one or more implementations are set forth in the accompanying drawings and the description below. Other features will be apparent from the description and drawings, and from the claims.

DESCRIPTION OF DRAWINGS

Like reference symbols in the various drawings indicate like elements.

DETAILED DESCRIPTION

Figure 1:
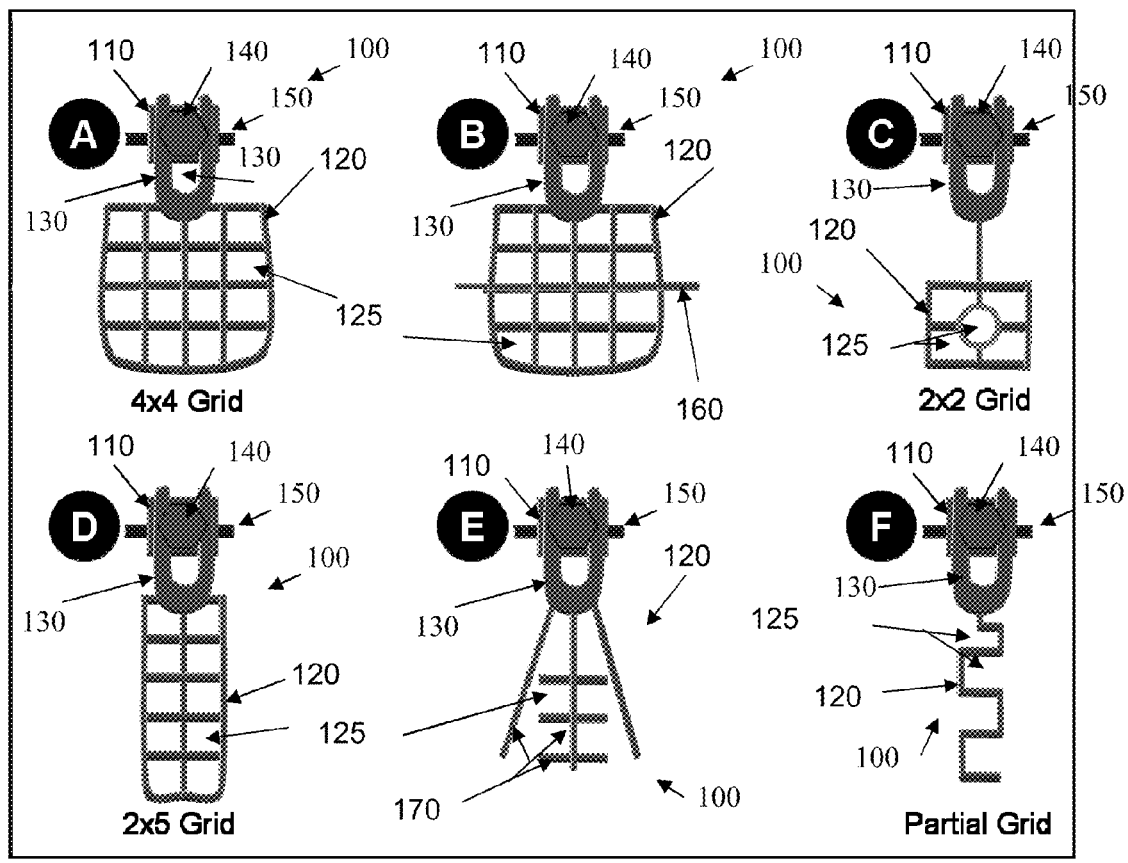
FIGS. 1A-G illustrate examples of orthodontic placement systems.

Systems, processes, and apparatus facilitate dental implant placement. Dental implants include, but are not limited to, screws, mini-screws, micro-screws, and/or micro-implants. Dental implants may be temporary, semi-permanent, or permanent. For example, dental implants, such as miniscrews, are often used as anchors in various orthodontic systems.

Incorrect and/or inaccurate placement of dental implants, such as miniscrews in the alveolar bone, may reduce the anchoring capabilities of a miniscrew and/or increase patient discomfort (e.g., contacting a nerve during miniscrew placement). The guide and/or placement system may increase the accuracy of dental implant placement.

The system includes one or more guides and/or placement systems. The system is positioned in a patient and a radiograph is obtained to determine the appropriate position for a dental implant. The appropriate position is marked on the patient with the guide in place. The guide and/or placement system may be removed and the dental implant (e.g., miniscrew) may be positioned in the patient.

A guide may be at least partially made of and/or coated with a radio-opaque material. For example, at least a portion of the guide may include stainless steel, other radio-opaque metals, radio-opaque dental resins, and/or combinations thereof. The use of a radio-opaque material in at least a portion of the guide allows at least these portions of the guide to be visible in radiographs.

The guide may include horizontal, vertical, and/or oblique members. The guide may be planar and/or curved. Curved guides may have a curvature similar to a portion of a mouth of a patient and may reduce patient discomfort during use.

The guide or portions thereof may be flexible and/or deformable. Deformable guides may be deformed to facilitate placement, to mock a curvature of a portion of a mouth of a patient, to reduce patient discomfort, or to accommodate a preference of the user.

In some implementations, the members of the guide may be individually or collectively deformed by a user. For example, the members may include stainless steel and be bent to fit the patient's anatomy and gingival structures. In addition, members may be adjusted in height as well as in the mesio-distal position to better fit the interradicular space.

In some implementations, the guides may include interchangeable members. Interchangeable members may allow a guide to better fit a patient, satisfy specific clinical needs, and/or satisfy individual doctor preferences. Interchangeable members may include members such as a double straight arm, a single straight arm, a grid with mucogingival junction indicator, and/or a single arm with aiming circle (e.g., in which the dental implant may be received).

The guide may also have a shape similar to a grid, an irregular grid, a partial grid, and/or combinations thereof. The guide may include circles, rectangles, lines, any other appropriate shapes, and/or combinations thereof.

The guide may include apertures (e.g., voids in the guide, voids formed by various members of the guide, voids formed adjacent or proximate to members, etc.). A user may mark a region of a body through an aperture of the guide when the guide is placed in a patient. For example, once a radiograph is obtained and an appropriate position for a miniscrew is determined, a user (e.g., a dentist or an oral surgeon) may mark the appropriate position through an aperture in the guide.

The apertures of a guide may have specified size(s) to facilitate accurate placement of a dental implant. As the size of an aperture of a guide increases, the accuracy of placement may decrease since determined appropriate position for a dental implant may include a nerve or other non-desired region (e.g., important structures of the teeth) if the aperture is too large. For example, apertures may have a size that is less than a miniscrew. The aperture may have a size large enough for a user to mark a region of a patient's gums, for example, while the guide is in use.

FIGS. 1A-1F illustrate examples of orthodontic systems 100. As illustrated, the orthodontic system includes a base 110 and a guide 120 coupled to the base using an adjustment member 130. The guide includes more than one positioning aperture 125. Utilizing a guide 120 with more than one positioning aperture 125 may facilitate positioning, since a guide may be positioned in a general area in which a dental implant may be disposed (e.g., as opposed to a guide with a single positioning aperture which must be placed accurately to ensure that the dental implant can be positioned at least partially through the aperture). The adjustment member 130 may include an adjustment aperture 125. The base 110 and/or coupling member 140 may be at least partially disposed in the adjustment aperture 125. The base 110 may be coupled (e.g., directly or indirectly) to an archwire 150 and thus coupled to a portion of a mouth (e.g., when an archwire is coupled to a segment of teeth via brackets). As illustrated in FIG. 1A, the guide 120 may have a grid-like shape. The guide may have curved members and linear members, as illustrated.

FIG. 1B illustrates another example of a guide 120. The guide 120 includes a mucogingival junction (MGJ) member 160, where the MGJ member 160 is radio-opaque, to indicate the MGJ during use. During use, the MGJ member 160 may be aligned or approximately aligned with the MGJ in a patient. Since the MGJ member 160 is visible to the eye but more difficult to identify in radiographs, using a guide 120 with an MGJ member 160 may facilitate identification of the MGJ in a patient. The position of an MGJ member 160 in a patient in a radiograph may facilitate identification of an appropriate position of a dental implant, since the MGJ often separates the soft, fleshy mucus membrane of the oral cavity and the tougher, collagen-rich gingiva. Although the MGJ member 160 is shown in combination with a grid-like guide 120, the MGJ member may be used in combination with differently shaped guides, such as the guides illustrated in FIGS. 1C, 1E, and 1F.

FIG. 1C illustrates another example guide 120. The illustrated guide 120 includes a combination of shapes forming a guide. In some implementations, a circular member of the guide 120 may identify an area the user believes is the appropriate position for the dental implant. The circular member may be larger than other portions and/or may allow insertion of at least a portion of the dental implant through the member. In other implementations, the circular member may have a similar size to other portions of the guide and/or may be sized to inhibit insertion of at least a portion of a dental implant through the guide.

The placement of a dental implant through the guide may be inhibited (e.g., the guide may be sized to inhibit dental implant placement through the guide), in some implementations, because when the guide is sized to allow placement of a dental implant through the guide, the aperture in the guide may have a size that reduces the accuracy of placement. For example, if a large aperture, through which a dental implant may be placed, is not positioned correctly before a radiograph is obtained, the aperture may include an undesirable area (e.g., a root, tooth structures, etc.), and the guide may need to be repositioned and a new radiograph obtained. This may increase the length and/or costs of the procedure. When guides include smaller apertures (e.g., smaller than the dental implant), an aperture from among the plurality of apertures in a guide may be identified that is the appropriate area and/or does not include undesirable areas. The appropriate area may be marked through the aperture, the guide may be removed, and the dental implant may be inserted.

A feature of guides with multiple apertures is that the placement of the guide may be less critical and thus performed by less skilled users (e.g., dental assistants, rather than dentists). The initial placement may be less critical since an appropriate position may be identified in any one of the multiple apertures, as opposed to guide with one aperture. When placement of the guide is simplified (e.g., can attach to existing archwires, can adhere to a tooth, and/or can be performed by a less skilled user), the length and/or the costs associated with the procedure may be reduced.

FIG. 1D illustrates another example of a guide 120. The guide 120 is a rectangular-shaped grid. In some implementations, based on the placement area of a patient and/or the skill of the user, more positioning apertures 125 may be desirable in the longitudinal direction, as opposed to the latitudinal direction. Patient comfort and/or a guide's 120 proximity to a patient's gums during use, for example, may be increased using a guide with more positioning apertures 125 in the longitudinal direction than the latitudinal direction. For example, since a patient's gums may be curved at the portion for placement of the dental implant, decreasing the width may decrease the size of the portion of the guide 120 that does not contact the gums. Increasing the size of the portion of the guide 120 that contacts the gums may increase the accuracy of the identification and/or the marking of the appropriate position for the dental implant in the patient (e.g., to minimize distortion effects and/or increase the ease of marking through the guide).

FIG. 1E illustrates an example guide 120. The guide 120 includes interchangeable members 170. The interchangeable members 170 may include vertical, horizontal (e.g., horizontal members, MGJ members, etc.), and oblique members. The members 170 may be coupled and/or contact other members. The positioning apertures (e.g., voids between members, recesses, etc.) formed by the various members may be of dissimilar sizes. The members may be deformable to obtain the desired angles between members in the guides.

FIG. 1F illustrates another example guide 120. The guide 120 illustrated includes vertical and horizontal members. The positioning apertures 125 (e.g., voids formed proximate members) may have similar or dissimilar sizes. A guide 120 similar to the illustrated guide may be used to determine the vertical coordinate of the appropriate position from a radiograph, when the horizontal position of an appropriate position is known or approximately known.

FIGS. 1A-1F illustrate various examples of shape guides; however, combinations of the examples and/or other appropriate shapes or combinations of shapes may be utilized in guides.

The guide may be positioned in a patient using a placement system. The guide may be removably couple-able to the placement system so that different guides may be used with the same placement system. This may allow the guides to be selected based on the application while using the same placement system.

The placement system may be non-invasive. Non-invasive systems may reduce patient discomfort and promote healing, since damage to surrounding tissue may be reduced. In addition, the non-invasive placement systems facilitate placement of the guide, since the placement systems may be positioned in a patient by dental assistants rather than doctors and dentists, which may reduce costs associated with dental implant placement.

Figure 1G:
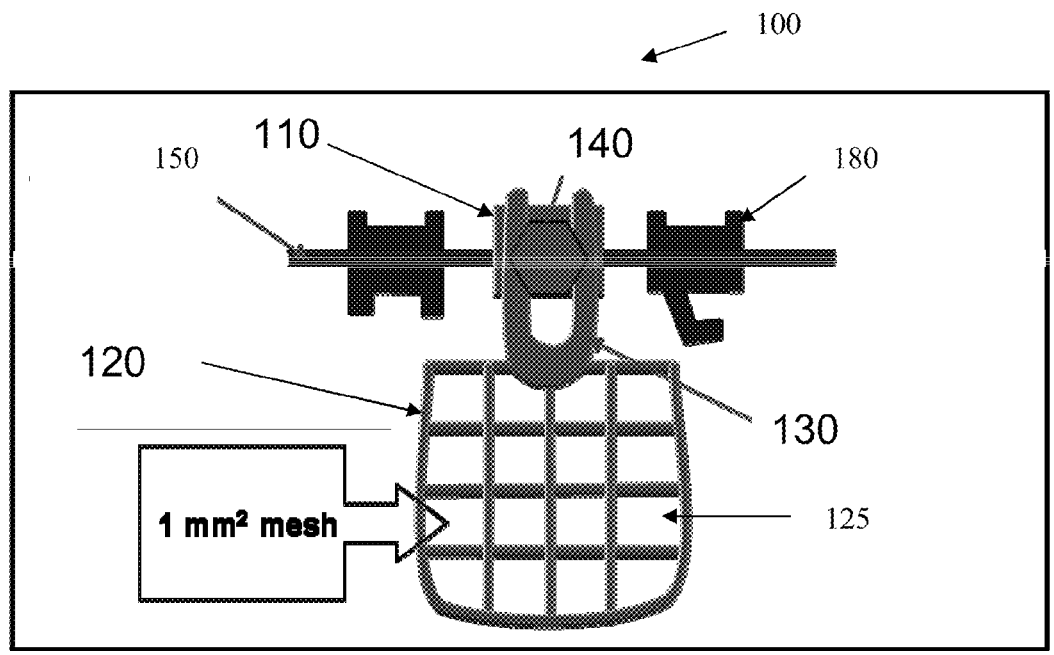

FIG. 1G illustrates an example orthodontic placement system 100. The orthodontic placement system 100 includes a base 110, an adjustment member 130, and/or a coupling member 140. The base 110 couples the placement system to an archwire 150 in a patient. The archwire may be pre-existing (e.g., a portion of orthodontic systems already positioned in a patient). Thus, by coupling the placement system to an existing archwire, the guide may be positioned and retained non-invasively. For example, temporary anchors in a patient's mouth may not be required to couple the guide to the desired position.

The base includes an aperture (e.g., a wire aperture, a coupling member aperture) through which the coupling member is received. The coupling member may be any appropriate fastener, such as a screw or brad. The base may also include a wire aperture in which the archwire is received. In some implementations, the wire aperture and the coupling member aperture may be similar, combined, portions of each other, discrete, etc. The wire aperture may be, for example, a slot, an indentation, or a recess in which the archwire is received. At least a portion of wire aperture may have a similar shape and/or size as at least a portion of the wire. For example, if a wire is substantially cylindrical, a portion of the wire aperture may have a similar curvature.

The placement system also includes an adjustment member. The adjustment member may couple the guide to the base. The adjustment member may be adjusted vertically relative to the base and rotated about the coupling member. Thus, a user may initially position the guide and then adjust the guide position vertically or horizontally by rotating the adjustment member and/or moving the adjustment member vertically. Utilizing an adjustment member that is capable of vertical and/or rotational movement may increase the flexibility of the system, since the placement system may be coupled to an available area of an archwire and the adjustment member may be adjusted to position the guide as desired. The coupling member may be tightened to retain the guide in the desired position.

Figure 2A:
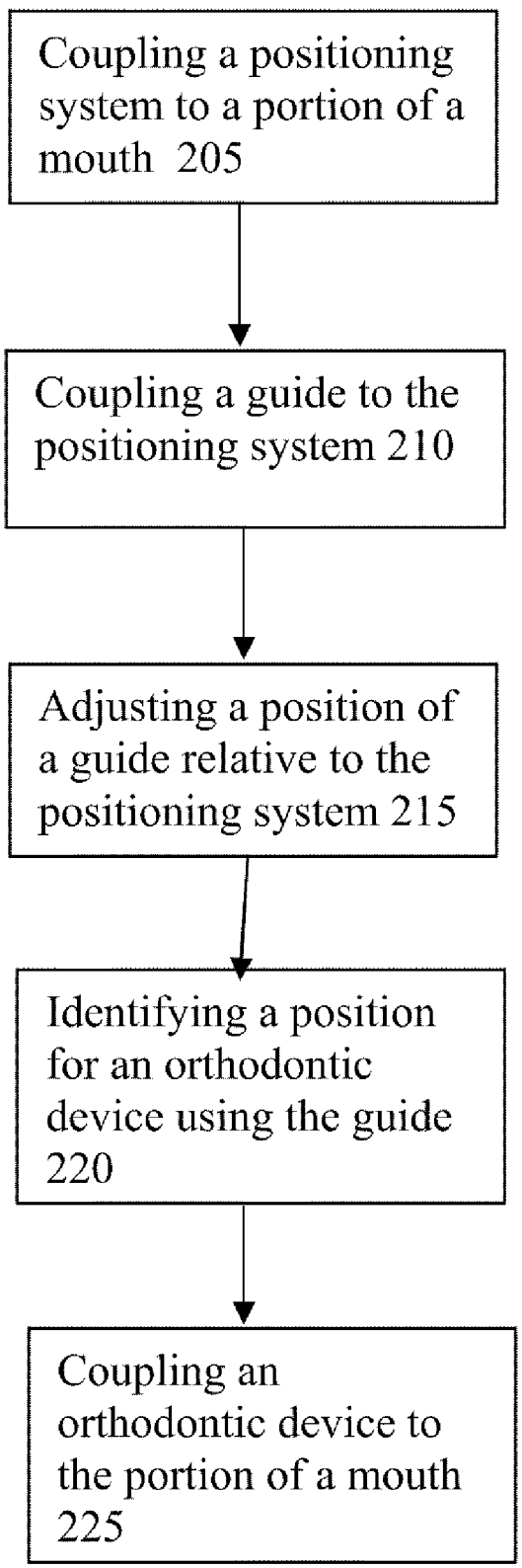
FIG. 2A illustrates a process for using an orthodontic placement system.

FIG. 2A illustrates an example process 200 for using an orthodontic placement system. Process 200 may be implemented by systems, such as systems 1A-G. A positioning system may be coupled to a portion of a mouth (operation 205). For example, a positioning system may include an acrylic base that is bonded to a portion of a patient's mouth (e.g., gums). The guide may be coupled to the positioning system (operation 210). For example, the guide may be directly (e.g., affixed, bonded, screwed) directly to the guide or indirectly (e.g., using an adjustment member) to a portion of a mouth (e.g., through the base). A position of the guide relative to the positioning system may be adjusted (operation 215). For example, a portion of a guide and/or adjustment member of the placement system may be at least partially deformable.

A position for an orthodontic device may be identified at least partially using the guide (operation 220). For example, a radiograph may be obtained of the system in a patient's mouth and an appropriate position for an orthodontic device may be identified (e.g., a portion without nerves, a portion with bones, and/or a portion that avoids other dental implants, etc.). The orthodontic device may be coupled to a portion of a mouth using the identified position (operation 225). For example, the orthodontic device (e.g., dental implant) may be positioned at least partially through an aperture of the guide, a dental implant may be positioned proximate a guide or through at least a portion of the guide.

In various implementations, operations may be added, deleted or modified. For example, a position of a guide relative to the positioning system may not be adjusted.

Figure 2B:
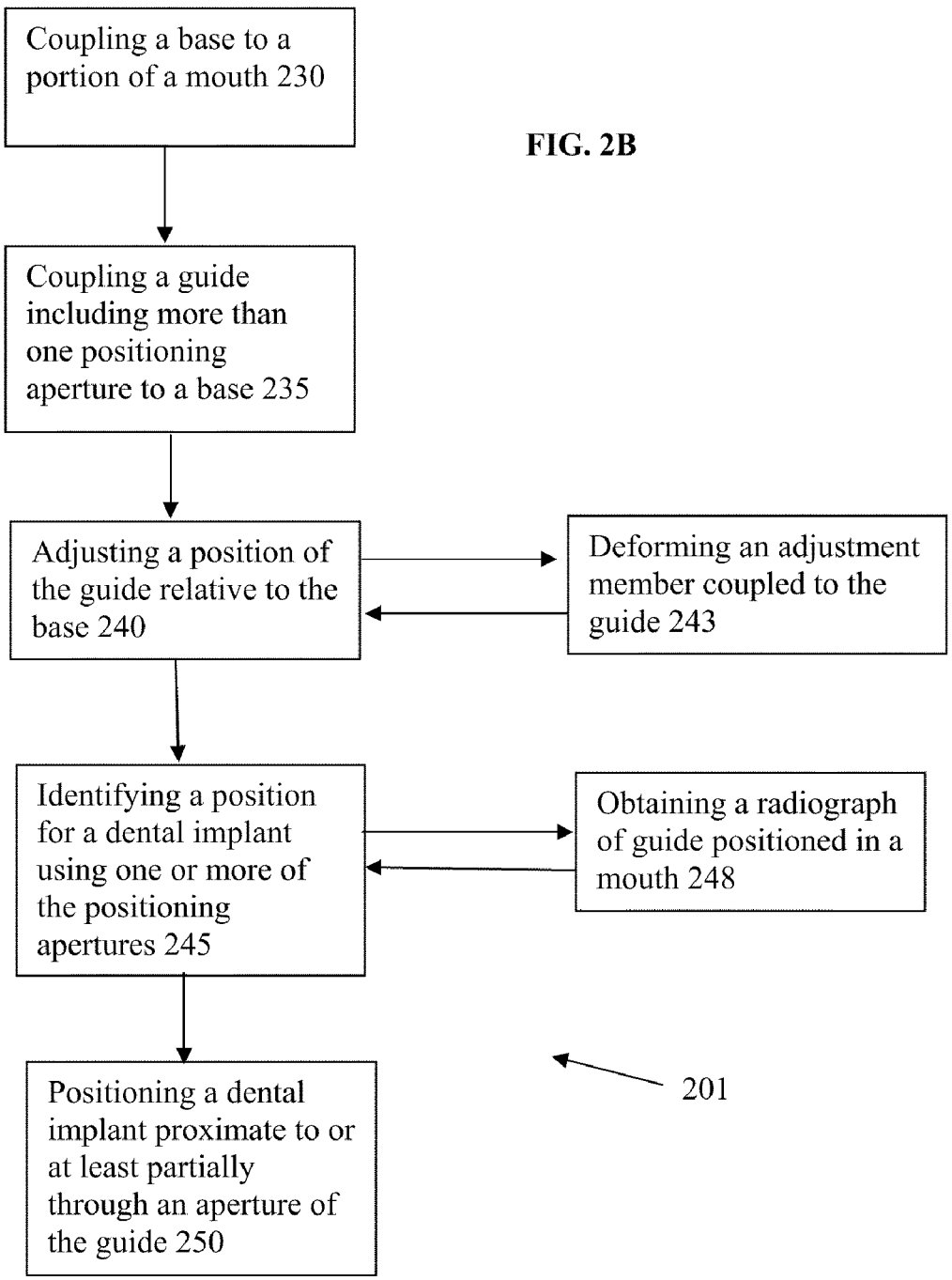
FIG. 2B illustrates a process for using an orthodontic placement system.

FIG. 2B illustrates an example process 201 for using a placement system. Various placement systems may be utilized such as systems illustrated in FIGS. 1A-1G. As illustrated, a base may be coupled to a portion of a mouth (e.g., directly or indirectly) (operation 230). For example, a base may be coupled to an archwire, which may be coupled to a bracket coupled to a segment of teeth to couple the base to a portion of a mouth. As another example, the base may be affixed, for example, to a portion of a mouth.

A guide that includes more than one positioning aperture may be coupled to the base (operation 235). For example, a coupling member may couple the guide and the base. As another example, a coupling member may couple an adjustment member coupled to the guide, to couple the base and the guide.

A position of the guide relative to the base may be adjusted (operation 240). At least a portion of the guide and/or adjustment member may be deformed or modified (operation 243). A position for a dental implant may be identified using one or more of the positioning apertures (operation 245). For example, an appropriate position for a dental implant may not contact nerves and/or contact bone. The identified position may inhibit significant nerve damage and/or contact bone. A radiograph may be obtained of the guide positioned in a mouth (operation 248). The radiograph may facilitate identification of the position for the dental implant.

A dental implant may be positioned proximate to or at least partially through an aperture of the guide (operation 250). For example, at least a portion of a dental implant may be positioned through a positioning aperture of the guide and coupled (e.g., bonded) to a portion of the mouth.

In various implementations, operations may be added, deleted, and/or modified. For example, the placement system or portions thereof may be removed from a patient's mouth after positioning and/or coupling of the dental implant in a portion of a mouth.

Figure 3A:
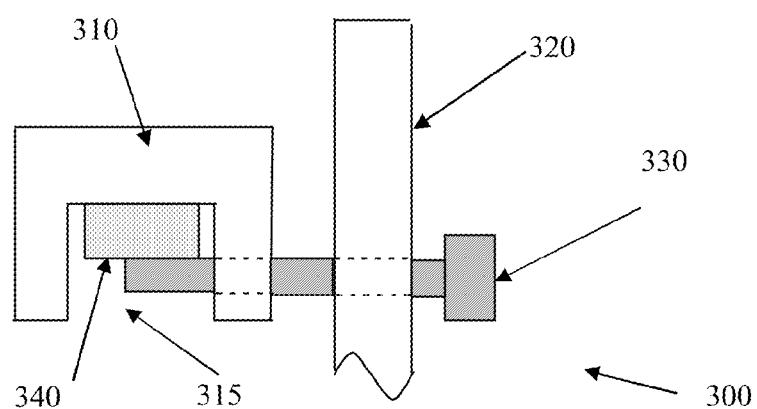
FIGS. 3A-C illustrate exploded views of portions of example placement systems.
Figure 3B:
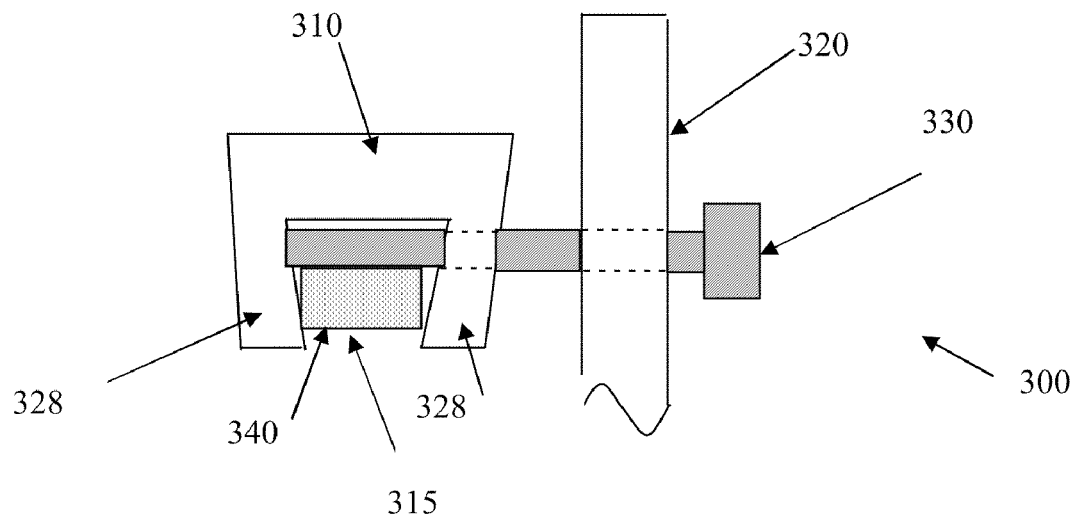
Figure 3C:
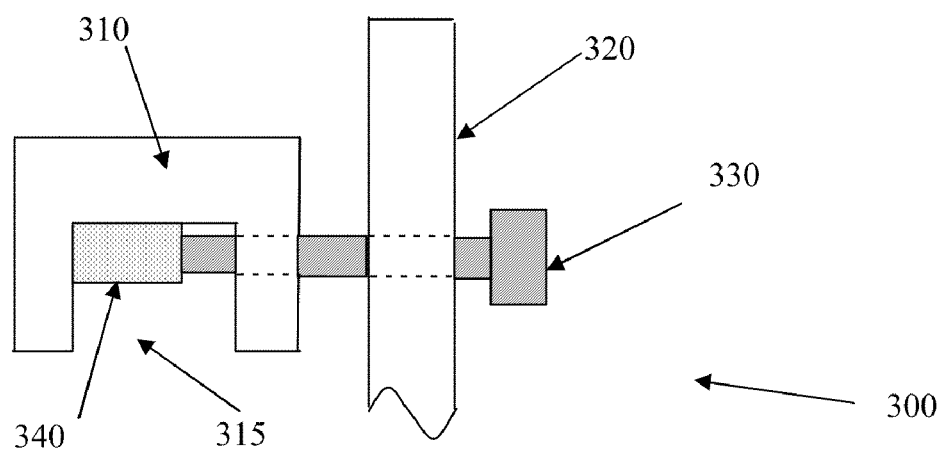

FIGS. 3A-C illustrate exploded views of portions of example placement systems 300. FIG. 3A illustrates an exploded view of a portion 300 of an example placement system. The coupling member aperture may pass through an adjustment member 320 and through or at least partially into the wire aperture 315 of the base 310. The coupling member 330 may retain the archwire 340 in the wire aperture 315, as illustrated. The archwire 340 may contact a surface of the wire aperture 315 in the base 310 during use and/or be retained in the wire aperture of the base using the coupling member 330.

FIG. 3B illustrates an exploded view of a portion 300 of another example placement system. The coupling member aperture may pass through or otherwise couple to the adjustment member. The coupling member may also pass through at least a portion of the base and the wire aperture of the base. Tightening the coupling member 330 may move protrusions 328 of the base 310 that at least partially form the wire aperture 315 towards each other. As the protrusions 328 of the base 310 are drawn towards each other, the walls of the protrusion may contact and retain an archwire 340 in the wire aperture. Thus, an archwire 340 in the wire aperture 315 may be retained by the base 310 even if the archwire is smaller than the wire aperture (e.g., a diameter of the archwire is less than the wire of the wire aperture) and archwires of various sizes may be accommodated by the base.

FIG. 3C illustrates an exploded view of a portion 300 of another example of a placement system. As illustrated in FIG. 3C, the archwire 340 may be retained in a wire aperture 315 of the base 310 using the coupling member 330. The coupling member 330 may pass through or other wise couple to the adjustment member and pass through at least a portion of the base 310. For example, the coupling member 330 may be received by a coupling aperture in the base. The coupling aperture may extend to the wire aperture. In the wire aperture, the coupling member may contact a surface of an archwire and retain the archwire in the wire aperture. Since the base may receive and retain archwires of different sizes (e.g., similarly sized or smaller than the wire aperture), archwires of various sizes may be accommodated by the wire aperture.

In some implementations, the wire aperture may retain archwires of various sizes (e.g., 0.022 inches or 0.018 inches). A feature of a wire aperture that retains archwires of various sizes is the ability to use the same placement system with various orthodontic systems. In other implementations, the wire aperture of the base may be sized to receive a specified range of archwire sizes (e.g., 0.15-0.20 inches).

Figure 4:
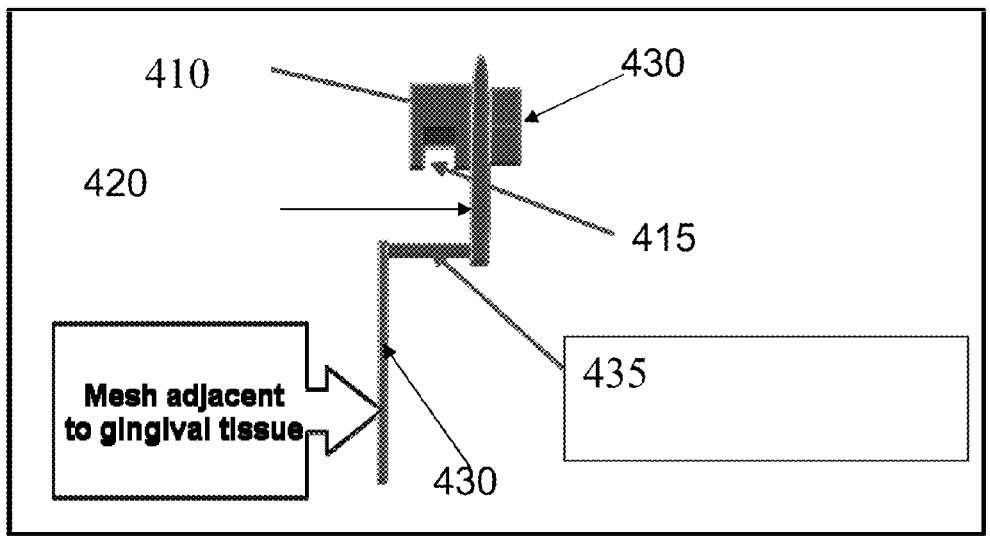
FIG. 4 illustrates a side view the example placement system illustrated in FIG. 2.

FIG. 4 illustrates a side view of the placement system illustrated in FIG. 2. The placement system may include a guide, a base with a wire aperture, an adjustment member, and/or a gingival adjustment inset. The coupling member may couple the base and the adjustment member. The gingival adjustment inset may couple the guide to the adjustment member. The gingival adjustment inset may allow the guide to be positioned closer to the gums, or other desired position in a patient, than without the inset. For example, during use the base member may be coupled to an archwire that is a specified distance from a surface of a tooth such that the base is disposed between the archwire and the tooth. The gingival adjustment inset may position the guide closer to the gums between the teeth, for example, than if the guide was coupled planar to the adjustment member. In some implementations, a gingival adjustment may not be utilized. For example, the guide may be coupled to the adjustment member and/or the base.

Figure 5:
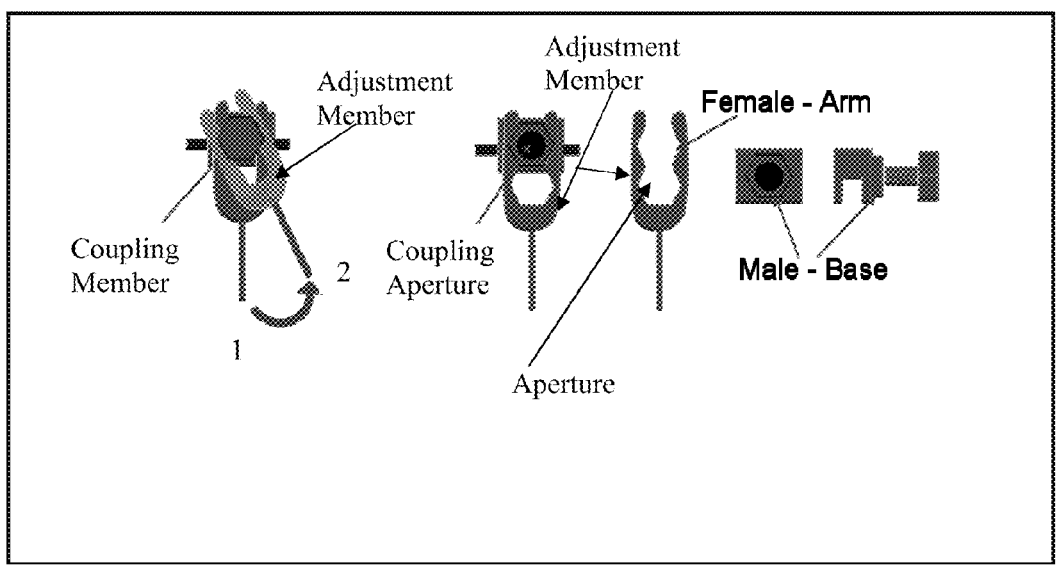
FIG. 5 illustrates examples of placement systems.

FIG. 5 illustrates another example of a placement system. As illustrated, adjustment members may rotate and be vertically adjusted to adjust the horizontal and/or vertical position of the guide. In some implementations, as illustrated in FIG. 5, the adjustment member may inhibit vertical and rotational movement of the adjustment member using apertures in the adjustment member. At least a portion of an aperture of the adjustment member may have a shape similar to the shape of the base. Thus, the rotation of the adjustment member, when coupled to the base, may be inhibited by the base. For example, a base may have a cross-sectional shape similar to a hexagon and an adjustment member may have apertures in which at least a portion is similar to a hexagon. Thus, when a portion of the base is received by the aperture of the adjustment member, rotation and vertical movement of the adjustment member may be inhibited by the base. The adjustment member may include more than one aperture to allow the guide to be positioned at various vertical heights relative to the base. In addition, the apertures and base may have a shape that allows an adjustment member to be rotated at specified degrees relative to the base. For example, if the base and the adjustment member have square-like shapes, the adjustment member may be rotated at 90 degree intervals, and retained in the rotated position.

In some implementations, the base and the coupling member may be a one-piece system. For example, a screw may be fastened into, but only partially screwed out of, the base member. As another example, the coupling member and/or base may include a lock that secures the coupling member to the base, but allows the coupling member to screw into and partially out of the base member. When using a two-piece system (e.g., a base and a separate screw), a probability may exist that the coupling member can be dropped into the mouth of the patient during use. When a coupling member is dropped or otherwise released from the base (e.g., during attachment or removal of the placement system), the patient may swallow the coupling member and/or the user may have difficulty retrieving the coupling member. A one-piece system may reduce patient injury and/or facilitate use of the placement system, since the coupling member may not be dropped into the mouth of the patient during use.

In some implementations, the placement system may attach to one or more teeth in a patient's mouth, in addition to and/or rather than, archwire. For example, the placement system may include a bracket designed to couple to one or more teeth in a patient's mouth. The bracket may fit at least partially over and/or around one or more teeth. The guide may attach directly or indirectly to the bracket.

Figure 6:
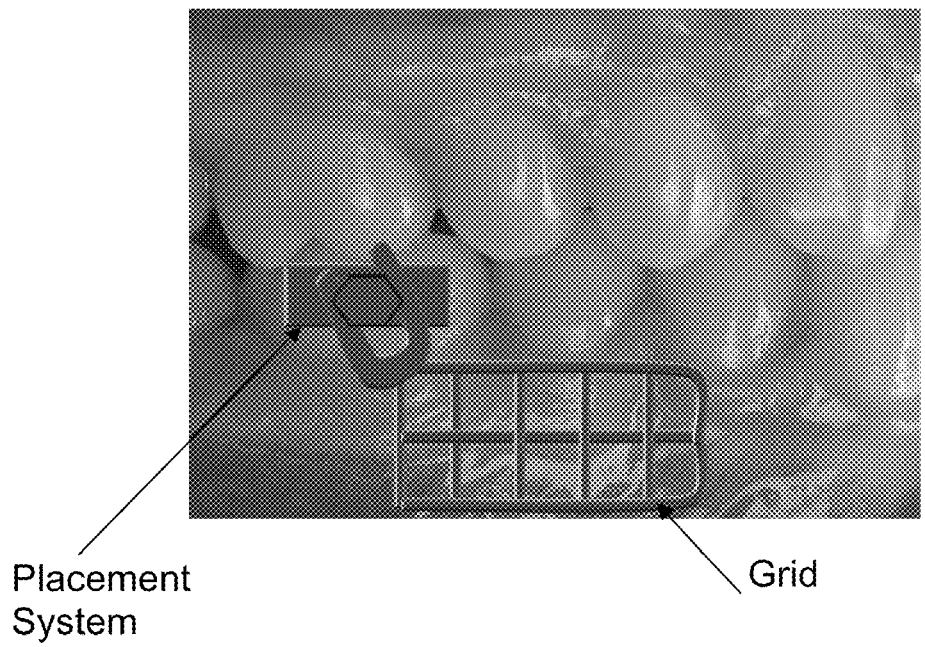
FIG. 6 illustrates an example of a placement system and guide in use.

The placement system may also include an acrylic base that contacts a patient's gums during use and retains the guide in position. The placement system may also couple to a desired area using an adhesive. For example, an adhesive may couple the placement system to a tooth or gums of a patient during use and the guide may be coupled to the placement system. FIG. 6 illustrates an example of a placement system coupled to a tooth. The illustrated placement system includes an adhesive that at least temporarily couples the placement system to a tooth. A similar placement system may be used to couple to gums.

Figure 7:
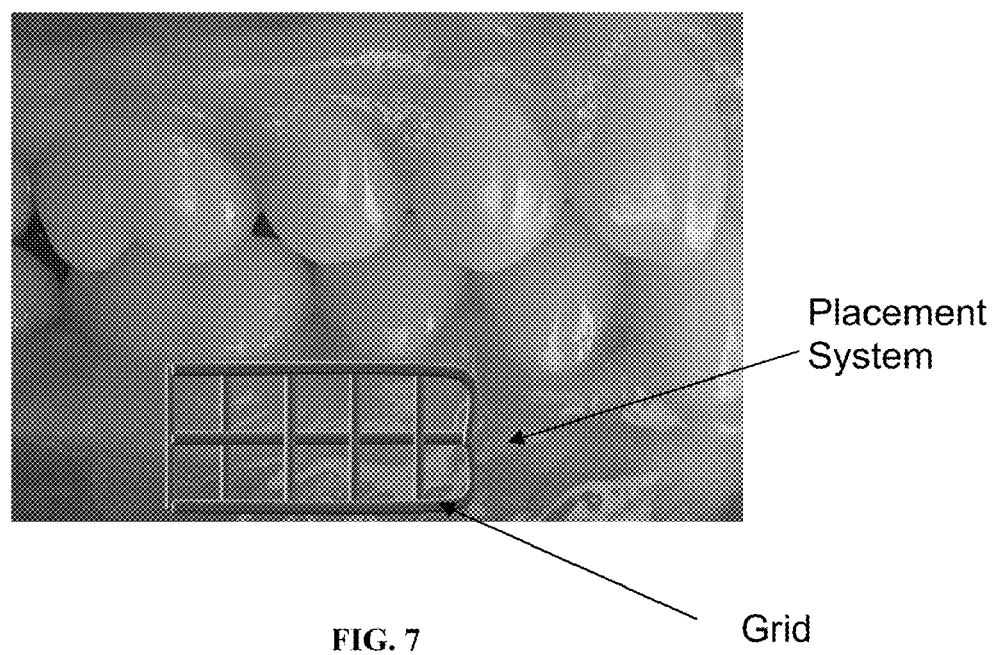
FIG. 7 illustrates an example of a placement system and guide in use.

The placement system may include an adhesive film or sheet, as illustrated in FIG. 7. The adhesive film may adhere to the gum, a tooth, or other desired placement area in a patient. The opposing side of the adhesive film may also couple directly or indirectly to a guide.

Although various placement systems have been described, the guide may be directly coupled to the patient during use. For example, the guide may be formed of material that frictionally is retained in position (e.g., on a patient's gums) during use. An adhesive may be utilized to retain a guide in position during use and/or the guide may include an adhesive coating to retain the guide in position during use.

Figure 8:
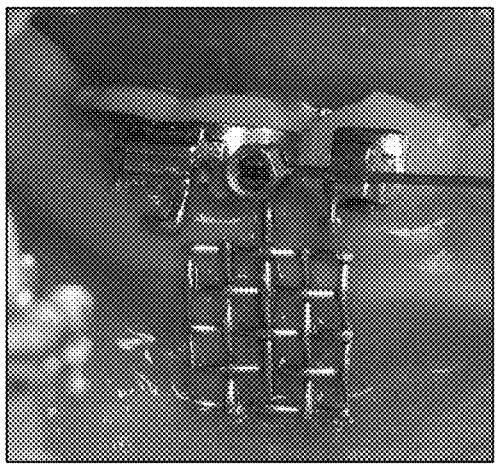
FIG. 8 illustrates an example of a placement system and guide in use.

During use of the system, a user determines the appropriate guide and placement system for the application. As illustrated in FIG. 8, the placement system is coupled to the archwire which is a portion of a patient's existing braces. The guide is also coupled to the patient using the placement system. The guide may be deformed such that it has a curvature similar to the portion of the patient's mouth where the guide will be placed. Although a placement system that utilizes a gurin lock is illustrated in FIG. 8, other types of placement systems may be utilized, such as the placement systems illustrated in FIGS. 1-7.

Figure 9:
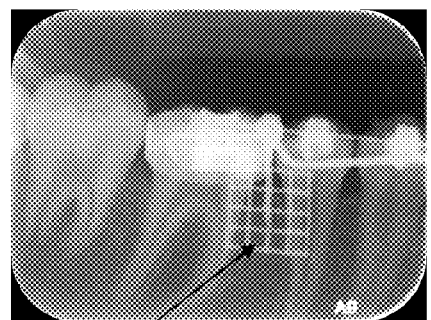
FIG. 9 illustrates an example of a radiograph of the example placement system and guide illustrated in FIG. 8.
Figure 10:
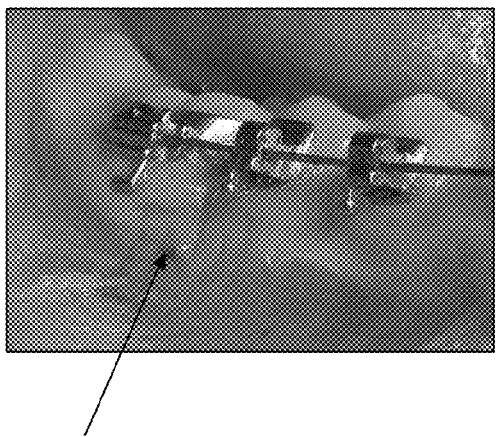
FIG. 10 illustrates an example of a marking for a dental miniscrew.
Figure 11:
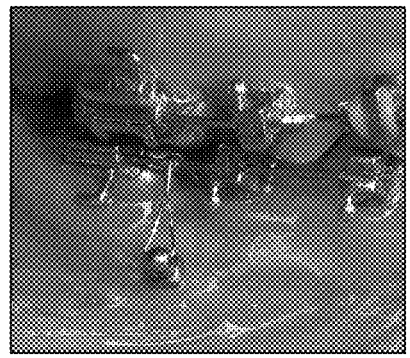
FIG. 11 illustrates an example of a miniscrew in use.

FIG. 9 illustrates an example of a radiograph obtained of the placement system illustrated in FIG. 8. As illustrated, the guide is visible and a user may determine the appropriate position for the dental implant (e.g., miniscrew). For example, the user may identify an area in which nondesirable portions (e.g., roots) are not present, such as the second box from the left in the bottom row of the grid, as indicated. The user may then mark the appropriate position, as illustrated in FIG. 10. The user may mark the position while the guide is in position and then may remove the guide for dental implant placement. As illustrated in FIG. 11, the dental implant may then be placed in the marked position.

Various implementations may include one or more of the following features. For example, the positioning accuracy of dental implants (e.g., miniscrews) in alveolar bone may be increased and/or the risks of injuring adjacent roots of teeth and periodontal structures during the dental implant procedure may be reduced. As another example, placement of the guides and/or placement systems may be performed by dental assistants and other less skilled users and/or by doctors and dentists. This may facilitate training and/or reduce procedure costs. As another example, the system may facilitate and/or increase the accuracy of the assessment of an appropriate position for the placement of miniscrew implants in alveolar and interradicular bone. Facilitating the assessment may increase the success of orthodontic procedures. Increasing accuracy may reduce patient complications during orthodontic procedures. In addition, the system may be sterilizable and/or autoclavable to satisfy government and/or industry regulations. The system and/or components of the system may be disposable. The system may also allow flexibility during use, since the placement system may couple to various locations along the orthodontic archwire. In addition, since the horizontal position of the guide may be adjusted using an adjustment member, the placement system may be positioned in an available space (e.g., free of other orthodontic attachments such as hooks and brackets) on the archwire and adjusted as desired by a user. In addition, since the guide includes various designs and/or may be flexible and/or deformable, the guides may be adapted to the application of the system and/or the preferences of the user. In some implementations, since the placement system is attached to the archwire, it is non-invasive, which may reduce patient discomfort and/or increase healing times. In some implementations, since the placement system is adhesively coupled to the patient, it is non-invasive, which may reduce patient discomfort and/or increase healing times. In addition, the system may reduce the length and cost of an orthodontic procedure since the process may only include minimal adjustments by the user (e.g., rather than trial and error placement, verified by multiple radiographs). Furthermore, users may be able to keep inventory low, which reduces costs since the placement systems and guides may be useable with a variety of orthodontic systems and/or members of the guides may be interchangeable and/or deformable. The process may be easily repeatable and/or accurate. In addition, once the system is positioned at a desired position, the system may be retained until removal or adjustment.

In various implementations, the systems, processes, and apparatus may be used on any site of the dental arch.

Several implementations for facilitating dental implant placement have been described, and a number of others have been mentioned or suggested. Furthermore, those skilled in the art will readily recognize that a variety of modifications, substitutions, deletions, and/or additions may be made to these implementations while still facilitating placement of dental implants. For example, in some implementations, the dental implant may be positioned in a patient while the guide and/or placement system is in place.

It is to be understood the implementations are not limited to particular systems or processes described, which may, of course, vary. It is also to be understood that the terminology used herein is for the purpose of describing particular implementations only, and is not intended to be limiting. As used in this specification, the singular forms "a", "an" and "the" include plural referents unless the content clearly indicates otherwise. Thus, for example, reference to "a grid" includes a combination of two or more grids and reference to "a marker" includes a combination of different types of markers.

What is claimed:

1. A method comprising:
   coupling a guide including a plurality of positioning apertures to a base;
   adjusting a position of the guide relative to the base; and
   identifying a position for a dental implant using one or more of the positioning apertures by obtaining a radiograph of the guide positioned in a mouth and marking the position based on a position of the positioning apertures.

2. The method of claim 1 further comprising coupling the base to a portion of a mouth.

3. The method of claim 1 wherein adjusting a position of the guide relative to the base includes deforming an adjustment member coupled to the guide, wherein the adjustment member couples the guide to the base.

4. The method of claim 1 further comprising disposing a dental implant proximate to or at least partially through an aperture of the guide.

* * * * *